United States Patent
Morton et al.

(10) Patent No.: US 7,842,630 B2
(45) Date of Patent: *Nov. 30, 2010

(54) WETTABLE POLYESTER FIBERS AND FABRICS

(75) Inventors: Colin J. H. Morton, Riehen (CH); Thomas Thompson, Highland Mills, NY (US); Ashutosh H. Sharma, Wappingers Falls, NY (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 40 days.

This patent is subject to a terminal disclaimer.

(21) Appl. No.: 11/985,118

(22) Filed: Nov. 14, 2007

(65) Prior Publication Data

US 2008/0064285 A1   Mar. 13, 2008

Related U.S. Application Data

(63) Continuation of application No. 11/185,993, filed on Jul. 20, 2005, now Pat. No. 7,314,839.

(60) Provisional application No. 60/590,545, filed on Jul. 23, 2004.

(51) Int. Cl.
   *D04H 1/00* (2006.01)
   *D04H 5/00* (2006.01)
   *B32B 25/02* (2006.01)

(52) U.S. Cl. .................. 442/361; 442/333; 428/296.1

(58) Field of Classification Search .............. 442/333, 442/361
   See application file for complete search history.

(56) References Cited

U.S. PATENT DOCUMENTS

| 4,336,307 | A | 6/1982 | Shiozaki et al. | 428/398 |
|---|---|---|---|---|
| 4,351,738 | A | 9/1982 | Takahashi et al. | 252/8.75 |
| 4,357,390 | A | 11/1982 | Ozaki et al. | 428/398 |
| 4,666,764 | A | 5/1987 | Kobayashi et al. | 428/254 |
| 4,713,408 | A | 12/1987 | Takahashi et al. | 524/161 |
| 4,745,142 | A | 5/1988 | Ohwaki et al. | 524/87 |
| 4,791,158 | A | 12/1988 | Lansberg et al. | 524/156 |
| 4,965,338 | A | 10/1990 | Tabankia et al. | 528/272 |
| 5,882,780 | A | 3/1999 | Yamamura et al. | 428/229 |
| 7,314,839 | B2 * | 1/2008 | Morton et al. | 442/361 |
| 2004/0101684 | A1 | 5/2004 | Jen | 428/395 |
| 2007/0117482 | A1 * | 5/2007 | Sharma et al. | 442/59 |

FOREIGN PATENT DOCUMENTS

GB   1269740   4/1972

OTHER PUBLICATIONS

English language abstract for JP 8060488 (Mar. 5, 1996).
English language abstract for JP 8260343 (Oct. 8, 1996).
English language abstract for JP 8260344 (Oct. 8, 1996).
English language abstract for JP 8260349 (Oct. 8, 1996).
English language abstract for JP 9077963 (Mar. 25, 1997).
English language abstract for JP 100925623 (Jan. 27, 1998).
English language abstract for JP 58081616 (May 17, 1983).

* cited by examiner

*Primary Examiner*—Lynda Salvatore
(74) *Attorney, Agent, or Firm*—Tyler A. Stevenson

(57) ABSTRACT

The present invention is aimed at a method of providing wettability to polyester fibers or filaments, to woven or non-woven fabrics made therefrom and to resultant articles of manufacture. The method comprises melt extruding a mixture comprising a polyester and one or more alkyl metal sulfonates where the metal is Na, Li or K and the alkyl is straight or branched chain alkyl of 12 to 15 carbon atoms, or is straight or branched chain alkenyl of 12 to 18 carbon atoms. The alkyl metal sulfonates are present from about 2% to about 5% by weight based on the weight of the polyester. A post treatment step such as an alkaline treatment step is not included. The melt extrusion mixtures do not include certain additives such as polyoxyalkylene compounds, alkylmonoethonolamide compounds, alkyldiethanolamine compounds and polyetheramide compounds.

11 Claims, No Drawings

WETTABLE POLYESTER FIBERS AND FABRICS

This application is a continuation of U.S. application Ser. No. 11/185,993, filed Jul. 20, 2005, now U.S. Pat. No. 7,314, 839, which claims the benefit under 35 USC 119(e) of U.S. provisional application No. 60/590,545, filed Jul. 23, 2004, the disclosures of which are hereby incorporated by reference.

The present invention relates to a method of providing polyester knit, woven or nonwoven fabrics with durable wettability and to the articles of manufacture prepared therefrom.

BACKGROUND

U.S. Pat. No. 4,357,390 teaches hollow polyester fibers with antistatic properties.

U.S. Pat. No. 4,351,738 teaches polyester filamentary yarns for high-speed friction draw-false twist texturing.

U.S. Pat. No. 4,666,764 discloses an antistatic polyester fabric having water repellency.

JP08060488, JP08260343, JP08260344, JP08260349, JP09077963, JP10025623 and JP58081616 disclose polyester fibers or fabrics with certain desirable properties.

It has surprisingly been found that melt blending polyester with certain alkyl metal sulfonates, and extruding the mixture into fibers, provides for polyester fibers or filaments with durable wettability and superior moisture management properties.

SUMMARY OF THE INVENTION

Disclosed are articles of manufacture that comprise a wettable polyester fabric which fabric comprises fibers or filaments which fibers or filaments comprise a melt blend which comprises a polyester and one or more alkyl metal sulfonates of the formula $RSO_3M$, where M is Na, K or Li and R is straight or branched chain alkyl of 12 to 15 carbon atoms or is straight or branched chain alkenyl of 12 to 18 carbon atoms, where the alkyl metal sulfonates are present from about 2% to about 5% by weight, based on the weight of the polyester, and where the fibers or filaments are not post-treated.

Also disclosed is a method for preparing an article of manufacture, which method comprises constructing the article from one or more wettable fabric layers, which fabric layers are prepared by a method comprising melt extruding a mixture which comprises a polyester and one or more alkyl metal sulfonates of the formula $RSO_3M$, into a plurality of fibers or filaments and cooling the fibers or filaments, where M is Na, K or Li and R is straight or branched chain alkyl of 12 to 15 carbon atoms or is straight or branched chain alkenyl of 12 to 18 carbon atoms, where the alkyl metal sulfonates are present from about 2% to about 5% by weight, based on the weight of the polyester, and where a post treatment step of the fibers or filaments is not included.

DETAILED DISCLOSURE

Post treatment steps include chemical, gas, plasma discharge, corona or alkaline treatment steps. Alkaline treatment steps are discussed for example in Textile Progress, Vol. 20, No. 2, Surface Modification of Polyester by Alkaline Treatments, pp. 13-14. Referenced within for example are U.S. Pat. Nos. 2,590,402, 2,828,528 and 3,135,577. Alkaline treatment steps are well known.

Other additional surface active agents are not required for the present articles of manufacture.

The present melt extrusion process does not include the presence of polyoxyalkylene additive compounds or polyoxyalkylene containing compounds. For example, the present compositions do not include polyethylene glycol (PEG), polypropylene glycol, or other polyoxyalkylene compounds (polyalkoxylates or polyalkylene glycols). Polyoxyalkylene containing compounds means for example alkyl polyalkoxylates, such as stearyl polyethylene glycol.

The present melt extrusion process does not include the presence of alkylmonoethanolamide or alkyldiethanolamine additive compounds.

The present melt extrusion process does not include the presence of polyetheramide additive compounds. Polyetheramide compounds means for example polyetheresteramide additive compounds and polyetherpolyamide additive compounds.

Polyetherpolyamides are disclosed for example in U.S. Pat. Nos. 5,140,065 and 4,356,300. The polyetherpolyamides are the products formed from the polycondensation of polyetherdiamines, dicarboxylic acids, dimeric acids and from lactams, for example caprolactam. The polyetherpolyamides are for example block copolymers. For instance, a polyetherpolyamide is formed from the polycondensation of caprolactam, a dimeric acid and a polyetherdiamine such as Jeffamine D-2000.

In a general sense, the polyetheresteramides known in the art comprise polyamide and polyether segments linked together with ester groups. They are prepared for example from polyamines, polybasic carboxylic acids and polyoxyalkylene glycols. In the simplest sense, they are a copolymer of a polyamide with carboxylic end groups (a dicarboxylic polyamide) and a polyoxyalkylene glycol.

Other surface active compounds not included are for example those disclosed in U.S. Pat. No. 5,882,780.

For example, all other surface active agents are excluded.

The present methods produce fibers or filaments, which are knitted, woven or bonded into knit, woven or nonwoven fabrics respectively.

The present melt extrusion methods form fibers or filaments. In accordance with known technology such as continuous filament spinning for yarn or staple fiber, and nonwoven processes such as spunbond production and meltblown production, the fibers or filaments are formed by extrusion of the molten polymer through small orifices. In general, the fibers or filaments thus formed are then drawn or elongated to induce molecular orientation and affect crystallinity, resulting in a reduction in diameter and an improvement in physical properties. In nonwoven processes such as spunbonding and meltblowing, the fibers or filaments are directly deposited onto a foraminous surface, such as a moving flat conveyor and are at least partially consolidated by any of a variety of bonding means. It is known to those skilled in the art to combine processes or the fabrics from different processes to produce composite fabrics which possess certain desirable characteristics. Examples of this are combining spunbond and meltblown to produce a laminate fabric. Additionally either or both of these processes may be combined in any arrangement with a staple fiber carding process or bonded fabrics resulting from a nonwoven staple fiber carding process. In such described laminate fabrics, the layers are generally at least partially consolidated.

The invention is also applicable to melt extruded bi-component fibers, wherein one of the components is a polyester according to this invention.

Nonwoven fabrics of polyester may have a carded fiber structure or comprise a mat in which the fibers or filaments are distributed in a random array. The fabric may be formed by any one of numerous known processes including hydroentanglement or spun-lace techniques, or by air laying or meltblowing filaments, batt drawing, stitchbonding, etc., depending upon the end use of the article to be made from the fabric.

Thermoplastic polyester fibers are typically extruded at temperatures in the range of from about 285° to about 300° C.

According to the present invention, a specific alkyl metal sulfonate is incorporated into a thermoplastic polyester, such as polyethylene terephthalate, in the melt, and is extruded with the polyester into the form of fibers and filaments which are then quenched, attenuated and formed into fabrics, either in a subsequent or concomitant processing step.

The alkyl metal sulfonate may be compounded with the polymer pellets which are to be melt extruded. To improve processing, the compound may be preformulated or compounded into a polyester which may also contain a filler, such as talc, and other traditional stabilizers.

The mixing of the alkyl metal sulfonate is done by mixing it into molten polymer by commonly used techniques such as roll-milling, mixing in a Banbury type mixer, or mixing in an extruder barrel and the like. The heat history (time at which held at elevated temperature) can be shortened by mixing the alkyl metal sulfonate with unheated polymer particles so as to achieve substantially even distribution of the agent in the mass of polymer, thereby reducing the amount of time needed for intensive mixing at molten temperature.

Conveniently, the alkyl metal sulfonate can also be added substantially simultaneously or sequentially with any other additives which may be desired in certain instances. The alkyl metal sulfonate may also be preblended with other additives and the blend then added to the polymer. It is contemplated that in some instances the alkyl metal sulfonate may have the additional benefit of aiding the other additives to become more easily or evenly dispersed or dissolved in the polyester. For easier batch-to-batch control of quality, it may be preferred to employ concentrated masterbatches of polymer/additive blends which are subsequently blended, as portions, to additional quantities of polymer to achieve the final desired formulation. The masterbatch, or the neat additives, may be injected into freshly prepared polymer while the polymer is still molten and after it leaves the polymerization vessel or train, and blended therewith before the molten polymer is chilled to a solid or taken to further processing.

Accordingly, also disclosed is a present method which comprises preparing a masterbatch comprising one or more alkyl metal sulfonates and a first polyester and melt extruding a mixture which comprises said masterbatch and a second polyester into a plurality of fibers or filaments and cooling the fibers or filaments.

The present masterbatch, or concentrate, contains the alkyl metal sulfonates in a concentration of, for example, about 1% to about 75%, from about 2% to about 50%, from about 5% to about 40% by weight incorporated in a polyester.

The alkyl metal sulfonates, in total, are present in the methods of this invention from about 2% to about 5% by weight, based on the total weight of the polyester. For example, the alkyl metal sulfonates are present from about 2.5% to about 4.5%, from about 2.5% to about 5%, from about 2.5% to about 4%, from about 3% to about 4%, from about 3% to about 5%, or from about 3% to about 4.5%, based on the total weight of polyester. For instance, the present alkyl metal sulfonates are present at levels of about 2%, 2.5%, 3%, 3.5%, 4%, 4.5% or about 5%, based on the total weight of the polyester.

The incorporation of an alkyl metal sulfonate into a polyester fiber or filament according to the present invention results in observed improved wettability of these materials. This modification is also durable, such that the fibers or filaments and fabrics made therefrom do not lose their wettability upon aging or handling. The improved wettability is stable to repeated insults, without a loss of performance, even over extended time periods.

The present invention is aimed at nonwoven fabrics, for example polyester fabrics. It is also aimed at threads or yarns for weaving or knitting in conventional textile processes.

The alkyl metal sulfonates of the present invention are effective irrespective of other factors that influence the properties of nonwoven fabrics, for example, basis weight, fiber diameter, degree and type of bonding of the fibers, and the synergistic effects and influence of composite structures.

The present invention is not limited to single-component fibers. Polyester bi-component fibers, particularly side-by-side or sheath-core fibers would be expected to demonstrate the same practical benefits as single component fibers. It may be particularly efficacious to include the melt additive only in a single polyester component.

The present methods may be employed for hollow polyester fibers, for example as disclosed in U.S. Pat. Nos. 4,357,390 and 4,666,764, the relevant disclosures of which are hereby incorporated by reference. The disclosure of U.S. Pat. No. 4,351,738 is also incorporated by reference.

The fabrics of the present invention may be sterilized by exposure to about 0.5 to about 10 megarads of gamma irradiation. Sterilization with gamma irradiation is employed for hospital garments and the like.

Polyester woven and nonwoven fibers and fabrics prepared according to the present invention also exhibit exceptional printability.

The present fibers and fabrics according to this invention have excellent softness.

The polyester has dicarboxylic acid repeat units selected from the group consisting of aromatic dicarboxylic acids having 8 to 14 carbon atoms, aliphatic dicarboxylic acids having 4 to 12 carbon atoms, cycloaliphatic dicarboxylic acids having 8 to 12 carbon atoms, and mixtures thereof.

For instance such diacids are terephthalic acid, isophthalic acid, o-phthalic acid, naphthalene dicarboxylic acid, cyclohexane dicarboxylic acid, cyclohexanediacetic acid, diphenyl-4,4'-dicarboxylic acid, succinic acid, maleic acid, glutaric acid, adipic acid, sebacic acid and mixtures thereof.

For example diacids are terephthalic acid, isophthalic acid and 2,6-naphthalene dicarboxylic acid.

The diol or glycol portion of the polyester are derived from the generic formula HO-G-OH where G is an aliphatic, cycloaliphatic or aromatic moiety of 2 to 18 carbon atoms.

For example such diols or glycols are ethylene glycol, diethylene glycol, triethylene glycol, propane-1,3-diol, propane-1,2-diol, butane-1,4-diol, pentane-1,5-diol, hexane-1,6-diol, 1,4-cyclohexanedimethanol, 3-methylpentane-2,4-diol, 2-methylpentane1,4-diol, 2,2-diethyl-propane-1,3-diol, 1,4- di-(hydroxyethoxy)benzene, 2,2-bis(4-hydroxycyclohexyl)-propane, 2,4-dihydroxy-1,1,3,3-tetramethylcyclobutane, 2,2-bis-(3-hydroxyethoxyphenyl)propane, 2,2-bis-(4-hydroxypropoxyphenyl)ethane and mixtures thereof.

The diol is for example ethylene glycol or 1,4-cyclohexanedimethanol.

The polyester is for example poly(ethylene terephthalate) PET or poly(ethylene 2,6-naphthalene-2,6-dicarboxylate) PEN.

It is also contemplated that the polyester can also be a blend of polyesters or copolyesters including components mentioned above.

The present alkyl metal sulfonates are for example of the formula $RSO_3Na$ where R is straight or branched chain alkyl of 12 to 15 carbon atoms or is straight or branched chain alkenyl of 12 to 18 carbon atoms.

Alkenyl of 12 to 18 carbon atoms is for example oleyl.

The alkyl group is in particular a branched group. Branched means having secondary or tertiary carbon groups.

The compositions prepared by the methods of the invention may optionally also contain from about 0.01 to about 10%, preferably from about 0.025 to about 5%, and especially from about 0.1 to about 3% by weight of various conventional stabilizer coadditives, such as the materials listed below, or mixtures thereof.

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1-methylundec-1-yl)phenol, 2,4-dimethyl-6-(1-methylheptadec-1-yl)phenol, 2,4-dimethyl-6-(1-methyltridec-1-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl)adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl)disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3-tert-butyl-4-hydroxyphenyl)butyrate], bis(3-tert-butyl-4-hydroxy-5-methyl-phenyl)dicyclopentadiene, bis[2-(3'tert-butyl-2-hydroxy-5-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy-2-methylphenyl)pentane.

1.7. Benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, 1,3,5-tri-(3,5-di-tert-butyl-4-hydroxybenzyl)-2,4,6-trimethylbenzene, di-(3,5-di-tert-butyl-4-hydroxybenzyl)sulfide, 3,5-di-tert-butyl-4-hydroxybenzyl-mercapto-acetic acid isooctyl ester, bis-(4-tert-butyl-3-hydroxy-2,6-dimethylbenzyl)dithiol terephthalate, 1,3,5-tris-(3,5-di-tert-butyl-4-hydroxybenzyl) isocyanurate, 1,3,5-tris-(4-tert-butyl-3-hydroxy-2,6-dimethylbenzyl)isocyanurate, 3,5-di-tert-butyl-4-hydroxybenzyl-phosphoric acid dioctadecyl ester and 3,5-di-tert-butyl-4-hydroxybenzyl-phosphoric acid monoethyl ester, calcium-salt.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3,3-tetramethyl-butyl)phenyl]-2,2-bis(3,5-di-tert-butyl-4-hydroxybenzyl) malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris-(3,5-di-tert-butyl-4-hydroxyphenoxy)-1,2,3-triazine, 1,3,5-tris-(3,5-di-tert-butyl-4-hydroxy-benzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxy-lauric acid anilide, 4-hydroxy-stearic acid anilide, 2,4-bis-octylmercapto-6-(3,5-tert-butyl-4-hydroxyanilino)-s-triazine and octyl-N-(3,5-di-tert-butyl-4-hydroxyphenyl)-carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6- hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl) propionic acid with mono- or polyhydric alcohols, e.g. with methanol, ethanol, n-octanol, i-octanol, octadecanol, 1,6-hexane-diol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazide, N,N'-bis[2-(3-[3,5-di-tert-butyl-4-hydroxyphenyl] propionyloxy)ethyl]oxamide (Naugard®XL-1 supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenlenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis (4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino] ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyl-diphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octyl-phenothiazines, N-allylphenothiazin, N,N,N',N'-tetraphenyl-1,4-diaminobut-2-ene, N,N-bis-(2,2,6,6-tetramethyl-piperid-4-yl-hexamethylenediamine, bis(2,2,6,6-tetramethylpiperid-4-yl)-sebacate, 2,2,6,6-tetramethylpiperidin-4-one, 2,2,6,6-tetramethylpiperidin-4-ol.

2. UV absorbers and light stabilizers 2.1. 2-(2-Hydroxyphenyl)-2H-benzotriazoles, for example known commercial hydroxyphenyl-2H-benzotriazoles and benzotriazoles as disclosed in, U.S. Pat. Nos. 3,004,896; 3,055,896; 3,072,585; 3,074,910; 3,189,615; 3,218,332; 3,230,194; 4,127,586; 4,226,763; 4,275,004; 4,278,589; 4,315,848; 4,347,180; 4,383,863; 4,675,352; 4,681,905, 4,853,471; 5,268,450; 5,278,314; 5,280,124; 5,319,091; 5,410,071; 5,436,349; 5,516,914; 5,554,760; 5,563,242; 5,574,166; 5,607,987 and 5,977,219, such as 2-(2-hydroxy-5-methylphenyl)-2H-benzotriazole, 2-(3,5-di-t-butyl-2-hydroxyphenyl)-2H-benzotriazole, 2-(2-hydroxy-5-t-butylphenyl)-2H-benzotriazole, 2-(2-hydroxy-5-t-octylphenyl)-2H-benzotriazole, 5-chloro-2-(3,5-di-t-butyl-2-hydroxyphenyl)-2H-benzotriazole, 5-chloro-2-(3-t-butyl-2-hydroxy-5-methylphenyl)-2H-benzotriazole, 2-(3-sec-butyl-5-t-butyl-2-hydroxyphenyl)-2H-benzotriazole, 2-(2-hydroxy-4-octyloxyphenyl)-2H-benzotriazole, 2-(3,5-di-t-amyl-2-hydroxyphenyl)-2H-benzotriazole, 2-(3,5-bis-α-cumyl-2-hydroxyphenyl)-2H-benzotriazole, 2-(3-t-butyl-2-hydroxy-5-(2-(ω-hydroxy-octa-(ethyleneoxy)carbonyl-ethyl)-, phenyl)-2H-benzotriazole, 2-(3-dodecyl-2-hydroxy-5-methylphenyl)-2H-benzotriazole, 2-(3-t-butyl-2-hydroxy-5-(2-octyloxycarbonyl)ethylphenyl)-2H-benzotriazole, dodecylated 2-(2-hydroxy-5-methylphenyl)-2H-benzotriazole, 2-(3-t-butyl-2-hydroxy-5-(2-octyloxycarbonylethyl)phenyl)-5-chloro-2H-benzotriazole, 2-(3-tert-butyl-5-(2-(2-ethylhexyloxy)-carbonylethyl)-2-hydroxyphenyl)-5-chloro-2H-benzotriazole, 2-(3-t-butyl-2-hydroxy-5-(2-methoxycarbonylethyl)phenyl)-5-chloro-2H-benzotriazole, 2-(3-t-butyl-2-hydroxy-5-(2-methoxycarbonylethyl)phenyl)-2H-benzotriazole, 2-(3-t-butyl-5-(2-(2-ethylhexyloxy) carbonylethyl)-2-hydroxyphenyl)-2H-benzotriazole, 2-(3-t-butyl-2-hydroxy-5-(2-isooctyloxycarbonylethyl)phenyl-2H-benzotriazole, 2,2'-methylene-bis(4-t-octyl-(6-2H-benzotriazol-2-yl)phenol), 2-(2-hydroxy-3-α-cumyl-5-t-octylphenyl)-2H-benzotriazole, 2-(2-hydroxy-3-t-octyl-5-α-cumylphenyl)-2H-benzotriazole, 5-fluoro-2-(2-hydroxy-3,5-di-α-cumyl-phenyl)-2H-benzotriazole, 5-chloro-2-(2-hydroxy-3,5-di-α-cumylphenyl)-2H-benzotriazole, 5-chloro-2-(2-hydroxy-3-α-cumyl-5-t-octylphenyl)-2H-benzotriazole, 2-(3-t-butyl-2-hydroxy-5-(2-isooctyloxycarbonylethyl)phenyl)-5-chloro-2H-benzotriazole, 5-trifluoromethyl-2-(2-hydroxy-3-α-cumyl-5-t-octylphenyl)-2H-benzotriazole, 5-trifluoromethyl-2-(2-hydroxy-5-t-octylphenyl)-2H-benzotriazole, 5-trifluoromethyl-2-(2-hydroxy-3,5-di-t-octylphenyl)-2H-benzotriazole, methyl 3-(5-trifluoromethyl-2H-benzotriazol-2-yl)-5-t-butyl-4-hydroxyhydrocinnamate, 5-butylsulfonyl-2-(2-hydroxy-3-α-cumyl-5-t-octylphenyl)-2H-benzotriazole, 5-trifluoromethyl-2-(2-hydroxy-3-α-cumyl-5-t-butylphenyl)-2H-benzotriazole, 5-trifluoromethyl-2-(2-hydroxy-3,5-di-t- butylphenyl)-2H-benzotriazole, 5-trifluoromethyl-2-(2-hydroxy-3,5-di-α-cumylphenyl)-2H-benzotriazole, 5-butylsulfonyl-2-(2-hydroxy-3,5-di-t-butylphenyl)-2H-benzotriazole and 5-phenylsulfonyl-2-(2-hydroxy-3,5-di-t-butylphenyl)-2H-benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates and malonates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline, Sanduvor® PR25, dimethyl p-methoxybenzylidenemalonate (CAS #7443-25-6), and Sanduvor® PR31, di-(1,2,2,6,6-pentamethylpiperidin-4-yl)p-methoxybenzylidenemalonate (CAS #147783-69-5).

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amine stabilizers, for example 4-hydroxy-2,2,6,6-tetramethylpiperidine, 1-allyl-4-hydroxy-2,2,6,6-tetramethylpiperidine, 1-benzyl-4-hydroxy-2,2,6,6-tetramethylpiperidine, bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl)n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butane-tetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis-(2,2,6,6-tetramethyl-4-piperidyl)-hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis(2,2,6,6-tetramethyl-4-piperidyl)hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3,8-diaza-4-oxo-spiro[4,5] decane, a reaction product of 7,7,9,9-tetramethyl-2-cycloundecyl-1-oxa-3,8-diaza-4-oxospiro[4,5]decane and epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl)hexamethylenediamine, diester of 4-methoxy-methylene-malonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4-aminopiperidine.

The sterically hindered amine may also be one of the compounds described in U.S. Pat. No. 5,980,783, the relevant parts of which are hereby incorporated by reference, that is compounds of component I-a), I-b), I-c), I-d), I-e), I-f), I-g), I-h), I-i), I-j), I-k) or I-l), in particular the light stabilizer 1-a-1, 1-a-2, 1-b-1, 1-c-1, 1-c-2, 1-d-1, 1-d-2, 1-d-3, 1-e-1, 1-f-1, 1-g-1, 1-g-2 or 1-k-1 listed on columns 64-72 of said U.S. Pat. No. 5,980,783.

The sterically hindered amine may also be one of the compounds described in U.S. Pat. Nos. 6,046,304 and 6,297,299, the disclosures of which are hereby incorporated by reference, for example compounds as described in claims 10 or 38 or in Examples 1-12 or D-1 to D-5 therein.

2.7. Sterically hindered amines substituted on the N-atom by a hydroxy-substituted alkoxy group, for example compounds such as 1-(2-hydroxy-2-methylpropoxy)-4-octadecanoyloxy-2,2,6,6-tetramethylpiperidine, 1-(2-hydroxy-2-methylpropoxy)-4-hexadecanoyloxy-2,2,6,6-tetramethylpiperidine, the reaction product of 1-oxyl-4-hydroxy-2,2,6,6-tetramethylpiperidine with a carbon radical from t-amylalcohol, 1-(2-hydroxy-2-methylpropoxy)-4-hydroxy-2,2,6,6-tetramethylpiperidine, 1-(2-hydroxy-2-methylpropoxy)-4-oxo-2,2,6,6-tetramethylpiperidine, bis(1-(2-hydroxy-2-methylpropoxy)-2,2,6,6-tetramethylpiperidin-4-yl)sebacate, bis(1-(2-hydroxy-2-methylpropoxy)-2,2,6,6-tetramethylpiperidin-4-yl)adipate, bis(1-(2-hydroxy-2-methylpropoxy)-2,2,6,6-tetramethylpiperidin-4-yl) succinate, bis(1-(2-hydroxy-2-methylpropoxy)-2,2,6,6-tetramethylpiperidin-4-yl)glutarate and 2,4-bis{N-[1-(2-hydroxy-2-methylpropoxy)-2,2,6,6-tetramethylpiperidin-4-yl]-N-butylamino}-6-(2-hydroxyethyl-amino)-s-triazine.

2.8. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.9. Tris-aryl-o-hydroxyphenyl-s-triazines, for example known commercial tris-aryl-o-hydroxyphenyl-s-triazines and triazines as disclosed in, WO 96/28431, EP 434608, EP 941989, GB 2,317,893, U.S. Pat. Nos. 3,843,371; 4,619,956; 4,740,542; 5,096,489; 5,106,891; 5,298,067; 5,300,414; 5,354,794; 5,461,151; 5,476,937; 5,489,503; 5,543,518; 5,556,973; 5,597,854; 5,681,955; 5,726,309; 5,942,626; 5,959,008; 5,998,116 and 6,013,704, for example 4,6-bis-(2,4-dimethylphenyl)-2-(2-hydroxy-4-octyloxyphenyl)-s-triazine, Cyasorb® 1164, Cytec Corp, 4,6-bis-(2,4-dimethylphenyl)-2-(2,4-dihydroxyphenyl)-s-triazine, 2,4-bis(2,4-dihydroxyphenyl)-6-(4-chlorophenyl)-s-triazine, 2,4-bis[2-hydroxy-4-(2-hydroxy-ethoxy)phenyl]-6-(4-chlorophenyl)-s-triazine, 2,4-bis[2-hydroxy-4-(2-hydroxy-4-(2-hydroxyethoxy)phenyl]-6-(2,4-dimethylphenyl)-s-triazine, 2,4-bis[2-hydroxy-4-(2-hydroxyethoxy)phenyl]-6-(4-bromophenyl)-s-triazine, 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine, 2,4-bis(4-biphenylyl)-6-(2-hydroxy-4-octyloxycarbonylethylideneoxyphenyl)-s-triazine, 2-phenyl-4-[2-hydroxy-4-(3-sec-butyloxy-2-hydroxypropyloxy)phenyl]-6-[2-hydroxy-4-(3-sec-amyloxy-2-hydroxypropyloxy)-phenyl]-s-triazine, 2,4-bis(2,4-dimethylphenyl)-6-[2-hydroxy-4-(3-benzyloxy-2-hydroxy-propyloxy)phenyl]-s-triazine, 2,4-bis(2-hydroxy-4-n-butyloxyphenyl)-6-(2,4-di-n-butyloxyphenyl)-s-triazine, 2,4-bis(2,4-dimethylphenyl)-6-[2-hydroxy-4-(3-nonyloxy*-2-hydroxypropyloxy)-5-α-cumylphenyl]-s-triazine (* denotes a mixture of octyloxy, nonyloxy and decyloxy groups), methylenebis-{2,4-bis(2,4-dimethylphenyl)-6-[2-hydroxy-4-(3-butyloxy-2-hydroxypropoxy)-phenyl]-s-triazine}, methylene bridged dimer mixture bridged in the 3:5', 5:5' and 3:3' positions in a 5:4:1 ratio, 2,4,6-tris(2-hydroxy-4-isooctyloxycarbonylisopropylideneoxyphenyl)-s-triazine, 2,4-bis(2,4-dimethylphenyl)-6-(2-hydroxy-4-hexyloxy-5-α-cumylphenyl)-s-triazine, 2-(2,4,6-trimethyl-phenyl)-4,6-bis[2-hydroxy-4-(3-butyloxy-2-hydroxypropyloxy)phenyl]-s-triazine, 2,4,6-tris[2-hydroxy-4-(3-sec-butyloxy-2-hydroxypropyloxy)phenyl]-s-triazine, mixture of 4,6-bis-(2,4-dimethylphenyl)-2-(2-hydroxy-4-(3-dodecyloxy-2-hydroxypropoxy)-phenyl)-s-triazine and 4,6-bis-(2,4-dimethylphenyl)-2-(2-hydroxy-4-(3-tridecyloxy-2-hydroxypropoxy)-phenyl)-s-triazine, Tinuvin® 400, Ciba Specialty Chemicals Corp., 4,6-bis-(2,4-dimethylphenyl)-2-(2-hydroxy-4-(3-2-ethylhexyloxy)-2-hydroxypropoxy)-phenyl)-s-triazine and 4,6-diphenyl-2-(4-hexyloxy-2-hydroxyphenyl)-s-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl)phosphite, trilauryl phosphite, trioctadecyl phosphite, distearyl pentaerythritol diphosphite, tris (2,4-di-tert-butylphenyl)phosphite, diisodecyl pentaerythritol diphosphite, bis(2,4-di-tert-butylphenyl)pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl) pentaerythritol diphosphite, bis(2,4,6-tris(tert-butylphenyl) pentaerythritol diphosphite, tristearyl sorbitol triphosphite, tetrakis(2,4-di-tert-butylphenyl)4,4'-biphenylene diphosphonite, 6-isooctyloxy-2,4,8,10-tetra-tert-butyl-dibenzo[d,f][1,3,2]dioxaphosphepin, 6-fluoro-2,4,8,10-tetra-tert-butyl-12-methyl-dibenzo[d,g][1,3,2]dioxaphosphocin, bis(2,4-di-tert-butyl-6-methylphenyl)methyl phosphite, bis(2,4-di-tert-butyl-6-methylphenyl)ethyl phosphite, 2,2',2''-nitrilo[triethyltris(3,3',5,5'-tetra-tert-butyl-1,1'-biphenyl-2,2'-diyl) phosphite], 2-ethylhexyl(3,3',5,5'-tetra-tert-butyl-1,1'-biphenyl-2,2'-diyl)phosphite.

Especially preferred are the following phosphites:
Tris(2,4-di-tert-butylphenyl)phosphite (Irgafos®168, Ciba Specialty Chemicals Corp.), tris(nonylphenyl)phosphite, (A)
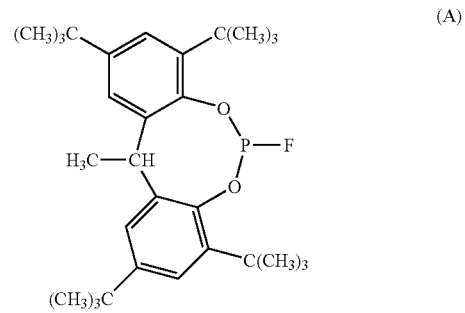

(B)
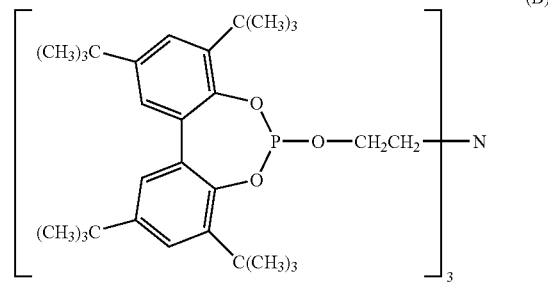

(C)
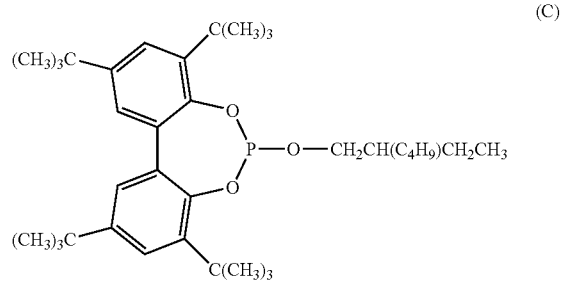

(D)
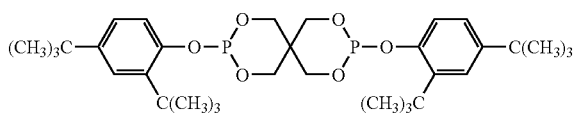

(E)
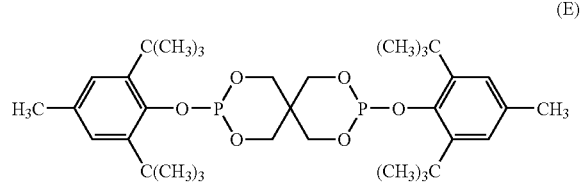

(F)
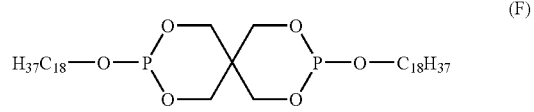

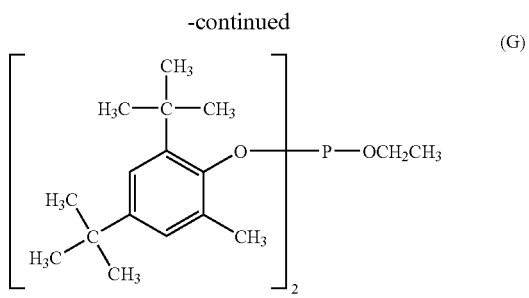

(G)

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxyl-amine, N-heptadecyl-N-octadecylhydroxylamine, N-methyl-N-octadecylhydroxylamine and the N,N-dialkylhydroxylamine derived from hydrogenated tallow amine.

6. Nitrones, for example N-benzyl-α-phenylnitrone, N-ethyl-α-methylnitrone, N-octyl-α-heptylnitrone, N-lauryl-α-undecylnitrone, N-tetradecyl-α-tridcylnitrone, N-hexadecyl-α-pentadecylnitrone, N-octadecyl-α-heptadecylnitrone, N-hexadecyl-α-heptadecylnitrone, N-ocatadecyl-α-pentadecylnitrone, N-heptadecyl-α-heptadecylnitrone, N-octadecyl-α-hexadecylnitrone, N-methyl-α-heptadecylnitrone and the nitrone derived from N,N-dialkylhydro-xylamine derived from hydrogenated tallow amine.

7. Amine oxides, for example amine oxide derivatives as disclosed in U.S. Pat. Nos. 5,844,029 and 5,880,191, didecyl methyl amine oxide, tridecyl amine oxide, tridodecyl amine oxide and trihexadecyl amine oxide.

8. Benzofuranones and indolinones, for example those disclosed in U.S. Pat. Nos. 4,325,863, 4,338,244, 5,175,312, 5,216,052, 5,252,643; DE-A-4316611; DE-A-4316622; DE-A-4316876; EP-A-0589839 or EP-A-0591102 or 3-[4-(2-acetoxyethoxy)-phenyl]-5,7-di-tert-butyl-benzofuran-2-one, 5,7-di-tert-butyl-3-[4-(2-stearoyloxyethoxy)phenyl]-benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, 3-(2-acetyl-5-isooctylphenyl)-5-isooctylbenzofuran-2-one, and 3-(2,3-dimethylphenyl)-5,7-di-tert-butyl-benzofuran-2-one.

9. Thiosynergists, for example dilauryl thiodipropionate or distearyl thiodipropionate.

10. Peroxide scavengers, for example esters of β-thiodipropionic acid, for example the lauryl, stearyl, myristyl or tridecyl esters, mercaptobenzimidazole or the zinc salt of 2-mercapto-benzimidazole, zinc dibutyldithiocarbamate, dioctadecyl disulfide, pentaerythritol tetrakis(β-dodecylmercapto)propionate.

11. Polyamide stabilizers, for example copper salts in combination with iodides and/or phosphorus compounds and salts of divalent manganese.

12. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example, calcium stearate, zinc stearate, magnesium behenate, magnesium stearate, sodium ricinoleate and potassium palmitate, antimony pyrocatecholate or zinc pyrocatecholate.

13. Nucleating agents, for example inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers).

14. Fillers and reinforcing agents, for example calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

15. Dispersing Agents, such as polyethylene oxide waxes or mineral oil.

16. Other additives, for example plasticizers, lubricants, emulsifiers, pigments, dyes, optical brighteners, rheology additives, catalysts, flow-control agents, slip agents, crosslinking agents, crosslinking boosters, halogen scavengers, smoke inhibitors, flameproofing agents, antistatic agents, clarifiers such as substituted and unsubstituted bisbenzylidene sorbitols, benzoxazinone UV absorbers such as 2,2'-p-phenylene-bis(3,1-benzoxazin-4-one), Cyasorb® 3638 (CAS #18600-59-4), and blowing agents.

The wettable fabrics produced from the fibers or filaments of this invention are particularly useful, for example, as the skin contacting inner lining fabric of sanitary articles of manufacture, particularly single use diapers, training pants, feminine hygiene products or incontinence care products. The fabrics also have utility in articles of manufacture such as wet and dry wipes, wound dressings, surgical capes, filter medial, battery separators, and the like.

The structure of diapers are described for example in U.S. Pat. Nos. 5,149,576, 5,961,504, 6,031,147 and 6,110,849, all incorporated herein by reference.

In addition, it is often desirable to impart wettability to melt extruded polyolefin films. Such films, in perforated form, are widely used as cover sheets for sanitary articles.

For coverstock for sanitary articles, improvements in wetback properties can be improved by the use of two or more layers of fabric bonded together. Examples include two spunbond layers or an SMS fabric in which the meltblown layer is devoid of the additive of formula (I).

The fabrics of the present invention may be sterilized by exposure to about 0.5 to about 10 megarads of gamma irradiation. Sterilization with gamma irradiation is employed for hospital garments and the like.

The following Examples further illustrate the invention. Unless otherwise indicated, amounts are reported as weight percent.

A mixture of polyethylene terephthalate (fiber grade, Wellman PERMACLEAR Lot 61458, 195 lb) and 5 lb of a mixture of primary and secondary sodium alkyl sulfonic acid salts $RSO_3Na$ where R=C14 (64%), C15 (31%) and C16 (5%) is prepared using a TURBULA Mixer Type T10B.

The mixture is then melt compounded using a Coperion Corporation Werner and Pfleiderer ZSK 25 mm twin screw extruder. The extruder heat zones are 220-230° C., screw speed 300 rpm, and feeder speed 40 lbs per hour. The molten polymer and additive exits via a four orifice round die. The molten material is immediately cooled and solidified in a cold water trough, then fed into a CONAIR/JETRO 304 pelletizer. The pellets are then pre-crystallized at 100° C. during 16 hours in a BLUE M forced air oven, the pellets are sieved and further dried in vacuo at 100° C. over 16 hours.

Nonwoven spunbond fiber samples are prepared from the 2.5% additive-PET pellets on a NORDSON FIBER SYSTEM/HILL INC. bicomponent spunbonding system under the following conditions:
Extruder temperature of 290-300° C.
Screen changer temperature of 300° C.
Spin head temperature of 300° C.
559 hole spinneret
Calander press with pressure of 800 PSI with top roll at 150° C. and bottom roll at 140° C.
Collection take up speed is adjusted to produce a nonwoven with a basis weight of 50 $gm^{-2}$ The resultant non-woven samples are evaluated for permeability and durability by measuring the liquid strikethrough time, according to the EDANA (European Disposables And Nonwovens Association) 150.4-99 standard test method on a Lenzing Lister 1997 model apparatus. This is the time for a known volume of simulated urine (9.0 g NaCl per litre) to pass through the nonwoven. The samples are also evaluated for continuous strikethrough on the same apparatus.

EDANA Liquid Strikethrough Time:
Test Method 150.4-99, results are in seconds with 3 readings per insult

| Blank PET (no additive) | 2.5% of $RSO_3Na$ additive |
|---|---|
| 100 seconds | 2.40 seconds |
| 100 seconds | 2.74 seconds |
| 100 seconds | 3.03 seconds |

The strikethrough data shows that the additive-PET composition provides a nonwoven polyethylene terephthalate fabric with excellent wettability.

EDANA Continuous Strikethrough Time:
Test Method 150.4-99, results are in seconds with 3 readings per insult
Maximum 30 seconds between passes, with test on identical nonwoven samples
Results are in seconds

|  | Blank PET (no additive) | with 2.5% additive |
|---|---|---|
| Pass 1 | >100, >100, >100 | 2.40, 2.74, 3.03 |
| Pass 2 | >100, >100, >100 | 3.04, 3.90, 3.62 |
| Pass 3 | >100, >100, >100 | 3.03, 2.80, 3.09 |
| Pass 4 | >100, >100, >100 | 3.31, 2.92, 2.93 |
| Pass 5 | >100, >100, >100 | 3.00, 2.87, 2.75 |
| Pass 6 | >100, >100, >100 | 2.74, 2.91, 2.60 |
| Pass 7 | >100, >100, >100 | 3.60, 3.16, 3.20 |
| Pass 8 | >100, >100, >100 | 2.64, 3.08, 2.59 |

The results of the continuous strikethrough test demonstrate that the compositions of the present invention are effective towards passing through repeated liquid insults with short time periods in between. It is a demonstration of the durability or permanence of the additive.

What is claimed is:

1. An article of manufacture that comprises a wettable polyester fabric
which fabric comprises fibers or filaments
which fibers or filaments comprise a melt blend which comprises
a polyester and one or more alkyl metal sulfonates of the formula $RSO_3M$,
where M is Na, K or Li and R is straight or branched chain alkyl of 12 to 15 carbon atoms or is straight or branched chain alkenyl of 12 to 18 carbon atoms,
where the alkyl metal sulfonates are present from about 2% to about 5% by weight, based on the weight of the polyester, and
where the fibers or filaments are not post-treated, and
where the melt blend does not contain surface active compounds selected from the group consisting of polyoxyalkylene additive compounds, alkylmonoethanolamide additive compounds, alkyldiethanolamine additive compounds and polyetheramide additive compounds.

2. An article according to claim 1, in which the polyester is poly(ethylene terephthalate) or poly(ethylene 2,6-naphthalene-2,6-dicarboxylate).

3. An article according to claim 1, in which the polyester is poly(ethylene terephthalate).

4. An article according to claim 1, in which the alkyl metal sulfonate is $RSO_3Na$.

5. An article according to claim 1, in which R is a branched chain alkyl or is a straight or branched chain alkenyl.

6. An article according to claim 1, in which R is oleyl.

7. An article according to claim 1, in which the alkyl metal sulfonates are present from about 2.5% to about 4.5% by weight, based on the weight of the polyester.

8. A method for preparing an article of manufacture,
which method comprises constructing the article from one or more wettable fabric layers,
which fabric layers are prepared by a method comprising melt extruding a mixture which comprises
a polyester and one or more alkyl metal sulfonates of the formula $RSO_3M$,
into a plurality of fibers or filaments and cooling the fibers or filaments,
where M is Na, K or Li and R is straight or branched chain alkyl of 12 to 15 carbon atoms or is straight or branched chain alkenyl of 12 to 18 carbon atoms,
where the alkyl metal sulfonates are present from about 2% to about 5% by weight, based on the weight of the polyester, and
where a post treatment step of the fibers or filaments is not included, and
where the mixture does not contain surface active compounds selected from the group consisting of polyoxyalkylene additive compounds, alkylmonoethanolamide additive compounds, alkyldiethanolamine additive compounds and polyetheramide additive compounds.

9. A method according to claim 8, further comprising bonding the fibers or filaments into a nonwoven fabric.

10. A method according to claim 8, which comprises
preparing a masterbatch comprising one or more alkyl metal sulfonates and a first polyester and
melt extruding a mixture which comprises said masterbatch and a second polyester
into a plurality of fibers or filaments and cooling the fibers or filaments.

11. An article of manufacture according to claim 1 selected from the group consisting of diapers, training pants, feminine hygiene products, incontinence care products, wet or dry wipes, wound dressings, surgical capes, filter medial and battery separators.

* * * * *